United States Patent
Huang et al.

(10) Patent No.: US 9,933,406 B2
(45) Date of Patent: Apr. 3, 2018

(54) SYSTEM AND METHODS FOR DETERMINING FOOD SPOILAGE

(71) Applicant: EatSafe LLC, San Diego, CA (US)

(72) Inventors: Norman Huang, San Diego, CA (US); Andrew Ong, Redwood City, CA (US)

(73) Assignee: EatSafe LLC, San Diego, CA (US)

( * ) Notice: Subject to any disclaimer, the term of this patent is extended or adjusted under 35 U.S.C. 154(b) by 0 days.

(21) Appl. No.: 15/159,644

(22) Filed: May 19, 2016

(65) Prior Publication Data
US 2016/0341709 A1 Nov. 24, 2016

Related U.S. Application Data
(60) Provisional application No. 62/163,612, filed on May 19, 2015.

(51) Int. Cl.
| | |
|---|---|
| *G05B 21/00* | (2006.01) |
| *G01N 33/02* | (2006.01) |
| *G01D 5/40* | (2006.01) |
| *C12Q 1/02* | (2006.01) |
| *H04W 4/00* | (2018.01) |

(52) U.S. Cl.
CPC ............. *G01N 33/02* (2013.01); *C12Q 1/02* (2013.01); *G01D 5/40* (2013.01); *H04W 4/005* (2013.01)

(58) Field of Classification Search
CPC .......................... G01N 21/783; G01N 21/3504
USPC ............................................. 422/83; 700/266
See application file for complete search history.

(56) References Cited

U.S. PATENT DOCUMENTS
| | | | |
|---|---|---|---|
| 6,537,802 B1 | 3/2003 | Alocilja et al. | |
| 2004/0115319 A1 | 6/2004 | Morris et al. | |
| 2006/0057022 A1 | 3/2006 | Williams et al. | |
| 2010/0100327 A1* | 4/2010 | Jensen | G01D 9/005 702/2 |
| 2014/0019067 A1 | 1/2014 | Potyrailo et al. | |
| 2015/0056099 A1 | 2/2015 | Peeters | |

FOREIGN PATENT DOCUMENTS
WO    WO 2013/096243 A1    6/2013

OTHER PUBLICATIONS
International Search Report and Written Opinion dated Aug. 26, 2016 for International Application No. PCT/US2016/033357, filed May 19, 2016, 16 pages.

* cited by examiner

*Primary Examiner* — Natalia Levkovich
(74) *Attorney, Agent, or Firm* — Kilpatrick Towsend & Stockton

(57) ABSTRACT

A food spoilage determination device is disclosed. The device includes a processor, an input device, an output device, and a memory. The device also includes a proximity sensor configured to determine a distance to a target and to communicate a distance signal to the processor, one or more environment sensors configured to determine one or more aspects of an environment of the target and to communicate one or more environment aspect signals to the processor, and one or more chemical sensors configured to determine one or more concentrations of one or more chemicals in the environment of the target and to communicate one or more chemical concentration signals to the processor. The processor is configured to determine food spoilage of the target based on the distance signal, the environment aspect signals, and the chemical concentration signals.

16 Claims, 7 Drawing Sheets

SYSTEM AND METHODS FOR DETERMINING FOOD SPOILAGE

CROSS-REFERENCES TO RELATED APPLICATIONS

This application claims the benefit of U.S. Provisional Application No. 62/163,612 filed May 19, 2015, titled "PORTABLE DEVICE FOR DETECTING FOOD SPOILAGE", the contents of which are incorporated herein by reference in their entirety for all purposes.

FIELD OF THE INVENTION

The present invention generally pertains to systems and methods of determining food spoilage, for example, with a portable device.

BACKGROUND OF THE INVENTION

The Center for Disease Control estimates that each year, roughly 48 million people get sick, 128,000 are hospitalized, and 3,000 die of food-borne diseases in the United States. According to a report published by Ohio State University, the economic burden to the United States costs up to $77.7 billion and does not include cost to the food industry. Victims most prone to food poisoning include older adults/physiologically sensitive individuals, families with pregnant women, infants, and/or young children, restaurants, and people traveling to foreign countries with little to no food regulation. Health-oriented consumers who are willing to pay more for safer and healthier food as indicated by their tendency to shop at high-end supermarkets are particularly in need of a handheld, contactless device that determines if a food item is safe for consumption via an electronic detection system that incorporates one or more gas sensors to determine spoilage of food.

BRIEF SUMMARY OF THE INVENTION

One inventive aspect is a food spoilage determination device. The device includes a processor, an input device configured to provide input signals to the processor, an output device configured to generate outputs based on output signals received from the processor, and a memory configured to receive information from and provide information to the processor. The device also includes a proximity sensor configured to determine a distance to a target and to communicate a distance signal to the processor, one or more environment sensors configured to determine one or more aspects of an environment of the target and to communicate one or more environment aspect signals to the processor, and one or more chemical sensors configured to determine one or more concentrations of one or more chemicals in the environment of the target and to communicate one or more chemical concentration signals to the processor. The processor is configured to determine food spoilage of the target based on the distance signal, the environment aspect signals, and the chemical concentration signals.

Another inventive aspect is a food spoilage determination system. The system includes a first device, including a processor, an input device configured to provide input signals to the processor, an output device configured to generate outputs based on output signals received from the processor, and a memory configured to receive information from and provide information to the processor. The system also includes a second device, including a proximity sensor configured to determine a distance to a target and to communicate a distance signal to the processor, one or more environment sensors configured to determine one or more aspects of an environment of the target and to communicate one or more environment aspect signals to the processor, and one or more chemical sensors configured to determine one or more concentrations of one or more chemicals in the environment of the target and to communicate one or more chemical concentration signals to the processor. The processor is configured to determine food spoilage of the target based on the distance signal, the environment aspect signals, and the chemical concentration signals.

DETAILED DESCRIPTION OF THE INVENTION

Particular embodiments of the invention are illustrated herein in conjunction with the drawings.

Various details are set forth herein as they relate to certain embodiments. However, the invention can also be implemented in ways which are different from those described herein. Modifications can be made to the discussed embodiments by those skilled in the art without departing from the invention. Therefore, the invention is not limited to particular embodiments disclosed herein.

Figure 1:
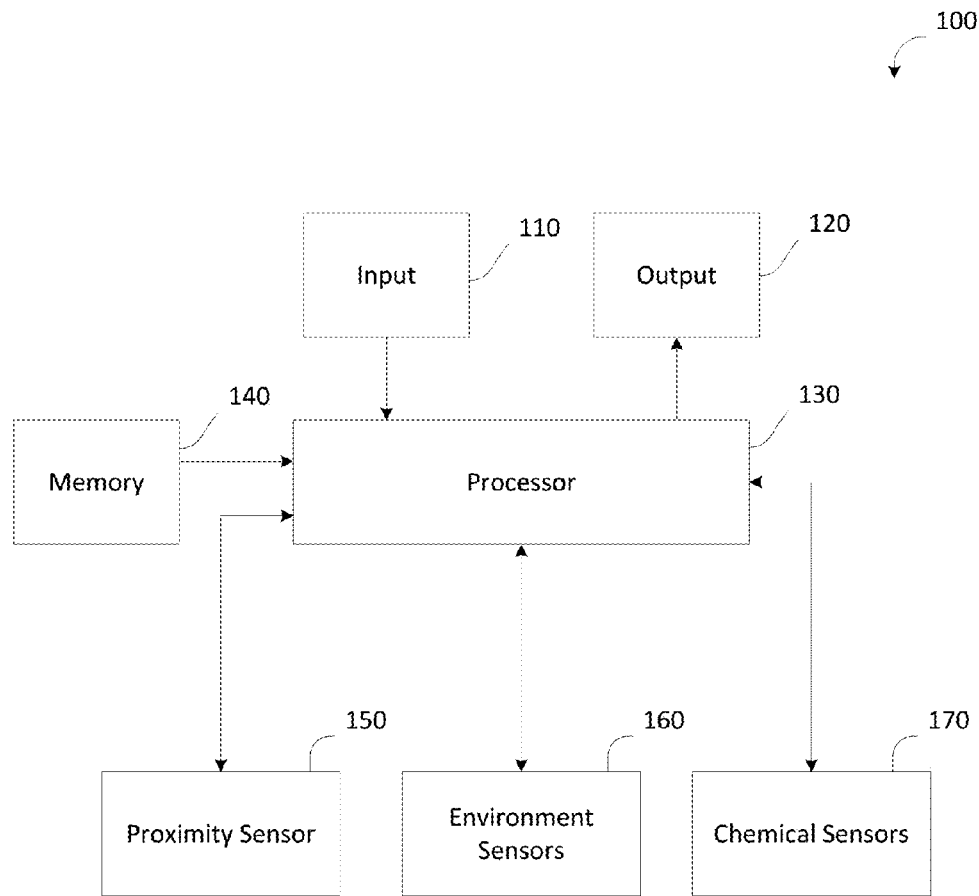
FIG. 1 is a schematic diagram of a system configured to determine food spoilage.

FIG. 1 is a schematic diagram of a food spoilage determination system 100 configured to determine food spoilage. System 100 includes input source 110 and output device 120, each connected with processor 130, which is in electrical communication with memory 140, proximity sensor 150, environment sensors 160, and chemical sensors 170.

Input source 100 may include, for example, one or more of a touchscreen display, one or more pressable mechanical buttons configured to selectively generate electronic signals, and another structure configured to receive commands from a user. Input source 100 is configured to receive input commands from a user and to generate electronic signals representing the commands. The electronic signals are transmitted to processor 130.

Output device 120 may include, for example, one or more of a graphic display, one or more light emitting devices, one or more sound emitting devices, and another output source. Output device 120 is configured to receive signals from processor 130, and to generate one or more outputs for a user representing or corresponding with the signals received from processor 130.

Proximity sensor 150 is configured to determine a proximity of a portion of system 100 to a target, and to generate one or more signals for processor 130 indicating the proximity. For example, proximity sensor 150 may be configured to determine a distance between the portion of the system 100 and a food item target, and to generate one or more signals representing a value of the distance. In some embodiments, proximity sensor 150 is an IR distance sensor.

Environment sensors 160 are configured to determine or measure one or more aspects of the environment of system 100. For example, environmental sensor 160 may include one or more thermometers and a humidity sensor. In some embodiments, environment sensors 160 include other sensors configured to determine or measure one or more at other aspects of the environment of system 100. For example, environment sensors 160 may include one or more of the following: an IR temperature sensor configured to determine a temperature of a target, such as food, and ambient temperature thermometer, and ambient humidity sensor, and airflow anemometer, a barometric pressure sensor, a noise sensor, and a gyrometer. Environment sensors 160 are also configured to generate one or more signals representing a value of each of the aspects determined or measured, and electrically communicate the determined or measured aspects to processor 130 via the signals.

Chemical sensors 170 are configured to determine or measure one or more concentrations of one or more chemicals in the environment of system 100. For example, chemical sensors 170 may include one or more of a reduction reaction sensor, an oxidation reaction sensor, and ammonia sensor, and an alcohol sensor. Chemical sensors 170 may additionally or alternatively include one or more other sensors configured to determine or measure one or more concentrations of one or more other chemicals in the environment of system 100.

In some embodiments, chemical sensors 170 may include one or more of a metal oxide sensor, an electrochemical sensor, a thermal conductivity sensor, a MEMS pellistor, an optical sensor, a carbon nanotube based sensor, a chemically sensitive conducting polymer film sensor, an antibody based molecule detection sensor, a nucleic acid detection sensor, and an IR sensor.

An electrochemical sensor may, for example, sense a concentration of one or more of the following chemical species: ethylene, $SO_2$, $O_2$, HS, and one or more other chemical species. An IR sensor may, for example, since a concentration of one or more hydrocarbons.

In some embodiments, chemical sensors 170 include one or more sensors which are configured to sense a concentration of only a single chemical species. For example, a carbon nanotube-based sensor may be configured to sense a concentration of only a specific chemical.

In some embodiments, chemical sensors 170 include one or more sensors configured to sense a concentration of volatile gasses and small molecular products, such as, but not limited to, ammonia, alcohol derivatives, carbon based sources (e.g. CO2, CO), nucleic acids, proteins markers, Acetaldehyde, Acetic Acid, Acetone, Acetonitrile, Acetylene, Acrylonitrile, Aldehydes, Alkanes, Alkenes, Alkynes, Aromatics, Benzene, Butadiene and other dienes, Butane, Butanol (n and isobutene), Carboxylic Acids, Chlorine Dioxide, Chloro-Compounds, Chloroethane, Cyclo-Hexane, Decane, DiEthylEther, Dienes, Diesel, Esters, Ethane, Ethers, Ethyl Acetate, Ethylamine, Ethylene, Ethylene Oxide, Formaldehyde, Helium, Hexane, Hydrogen Sulphide, Jet Fuel JP4, Methane, Methyl Ethyl Ketone (MEK), Methyl Methacrylate, Napthalene, Nitric Oxide, Nitrogen Dioxide, Octane, Oxygen, Ozone, Paraffin, Petrol, Phosphine, Propane, Propylene, Styrene, Sulfur Dioxide, Tetrahydrofuran (THF), Turpentine, VOC's, Vinyl Acetate, Vinyl Compounds, White Spirits, Xylene (ortho, meta and para).

In some embodiments, chemical sensors 170 include one or more sensors configured to sense a concentration of biological contaminants in food products such as those listed in the following table showing bacteria, food, and byproducts of the bacteria. In some embodiments, the concentration of a bacteria is sensed and deduced by the chemical sensors 170 sensing the concentrations of the byproducts associated with the bacteria.

| Bacteria | Food | Byproduct(s) |
|---|---|---|
| *Serratia marcescens* (N9) | Milk | Acetate<br>Ethanol<br>$CO_2$<br>Acetonin (3-hydroxy-2-butanone) |
| *Serratia proteamacufans* (O6a) | Milk | Acetate<br>Ethanol<br>Acetonin (3-hydroxy-2-butanone)<br>$CO_2$ |
| Mixed SM and SP | Milk | Acetate<br>Ethanol<br>Acetonin (3-hydroxy-2-butanone)<br>$CO_2$ |
| *Pseudomonas putida* (Try 16) | Milk | Acetate<br>$CO_2$ |
| *E. coli* (K12) | | $NH_3$ |
| *E. coli* ATCC 15490 | | $NH_3$ |
| *E. coli* ATCC 15992 | | $NH_3$ |
| *Enterobacter aerogenes* ATCC 13048 | | $NH_3$<br>$H_2S$ |
| *Pseudomonas aeruginosa* (ATCC 27853) | | ethyl (Et)<br>butyl (Bu)<br>hexyl (Hex)<br>octyl (Oct)<br>decyl (Dec)<br>$CF_3(CF_2)_3(CH_2)_2$—$(CF_4)$<br>$CF_3(CF_2)_5(CH_2)_2$—$(CF_6)$<br>$CF_3(CF_2)_7(CH_2)_2$—$(CF_8)$ |
| *Escherichia coli* (ATCC 25922) | | $NH_3$ |
| *Staphylococcus aureus* (ATCC 29213) | | |
| *Staphylococcus epidermidis* (ATCC 12228) | | |
| *E. coli* (DH10B strain) | | DMS (Dimethyl sulfide)<br>Ethanol<br>Methyl butanoate<br>Isoprene<br>Carbonyl sulfide (OCS)<br>Dimethyl disulfide (DMDS)<br>1-propanol |
| *Lactobacillus Lactococcus* Most streptococci | Dairy products | Lactic acid |
| Enterobacteriaceae | Animal intestines<br>Water or soil | lactic acid/lactate<br>acetic acid<br>formic acid<br>succinate/formate<br>ethanol<br>acetate<br>$CO_2$ & $H_2$ |
| Non-fecal enteric:<br>  *Klebsiella*<br>  *Enterobacter*<br>Fecal enteric:<br>  *E. coli*<br>  *Salmonella*<br>  *Shigella* | Gut flora | Same as above in addition to 2,3 butanedio which reacts with the acids to form acetonin |

-continued

| Bacteria | Food | Byproduct(s) |
|---|---|---|
| Clostridium acetobutylicum | Soil Intestines/ | Butanol/butric acid Acetone |
| Clostridia-type | raw meat & poultry | $H_2$ |
| Corynebacteria Propionibacterium Bifidobacterium | Swiss cheese | Propionate Acetic acid $CO_2$ Propionic acid |
| Acetobacter aceti | Vinegar | Ethanol |
| Leuconostoc mesenteroides | Wine (ruin) Fruit (Pink Disease) | Lactic Acid $CO_2$ Acetic acid $H_2$ |
| Agrobacterium tumefaciens Azotobacter vinelandii Pseudomonas aeruginosa Zymomonas mobilis | Alcohol Tequila | Ethanol $CO_2$ |
| Saccharomyces cerevisiae | Alcohol | Ethanol |
| Steptomyces | Vegetation Water (surface) Fish | $H_2O$ Geosmin |
| Pseudomonas denitrificans | Soil Animal intestines Water | $N_2$ $NO_2$ |
| Desulfovibrio desulfuricans | Water | S $H_2S$ |
| Methanococcus | Sea bed | Methane |

Chemical sensors 170 are also configured to generate one or more signals representing a value of each of the concentrations determined or measured, and electronically communicate the determined or measured concentrations to processor 130 with the signals.

Processor 130 is configured to receive commands from input source 110, and to generate outputs for output device 120 corresponding with and in response to the commands. Processor 130 is configured to interface with each of memory 140, proximity sensor 150, environment sensors 160, and chemical sensors 170. In response to commands received from input source 110, processor 130 is configured to provide commands to and receive information from memory 140, proximity sensor 150, environment sensors 160, and chemical sensors 170. Processor 130 is further configured to, in response to the commands received from input source 110, determine one or more outputs for output device 120 based on one or more calculations performed on the information received from memory 140, proximity sensor 150, environment sensors 160, and chemical sensors 170.

Figure 2:
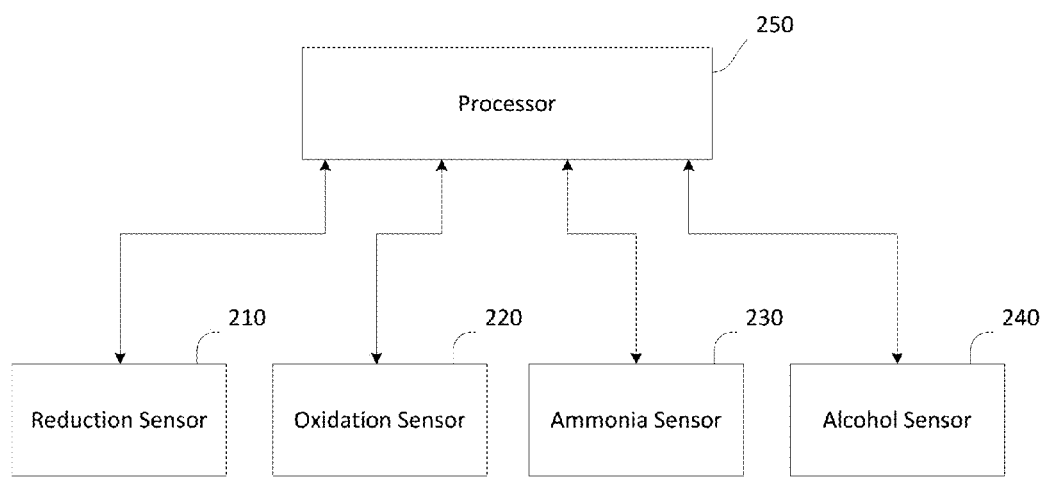
FIG. 2 is a schematic diagram illustrating exemplary chemical sensors which may be used in the system of FIG. 1.

FIG. 2 is a schematic diagram of exemplary chemical sensors which may be used in the system of FIG. 1. In the embodiment shown in FIG. 2, reduction reaction sensor 210, oxidation reaction sensor 220, ammonia sensor 230, and alcohol sensor 240 are each connected to processor 250. Processor 250 may be similar to or identical to processor 130 discussed above with reference to FIG. 1. In some embodiments, reduction reaction sensor 210, oxidation reaction sensor 220, ammonia sensor 230, and alcohol sensor 240 collectively constitute the chemical sensors 170 of FIG. 1.

Reduction reaction sensor 210 is configured to generate a signal corresponding with and representing a value of a concentration of one or more chemical species which react with the sensor in a chemical reduction reaction. In some embodiments, reduction reaction sensor 210 is configured to generate a signal indicating a concentration of one or more of the following chemical species: CO, $H_2S$, Butane, Propane, Methane, and one or more other species.

Oxidation reaction sensor 220 is configured to generate a signal corresponding with and representing a value of a concentration of one or more chemical species which react with the sensor in a chemical oxidation reaction. In some embodiments, oxidation reaction sensor 220 is configured to generate a signal indicating a concentration of one or more of the following chemical species: $NO_2$, NO, and Hydrogen, and one or more other species.

In some embodiments, other chemical sensors configured to determine or measure one or more concentrations of one or more other chemicals may be additionally or alternatively used. For example, sensors configured to detect one or more other chemicals listed herein may be additionally or alternatively used.

Figure 3:
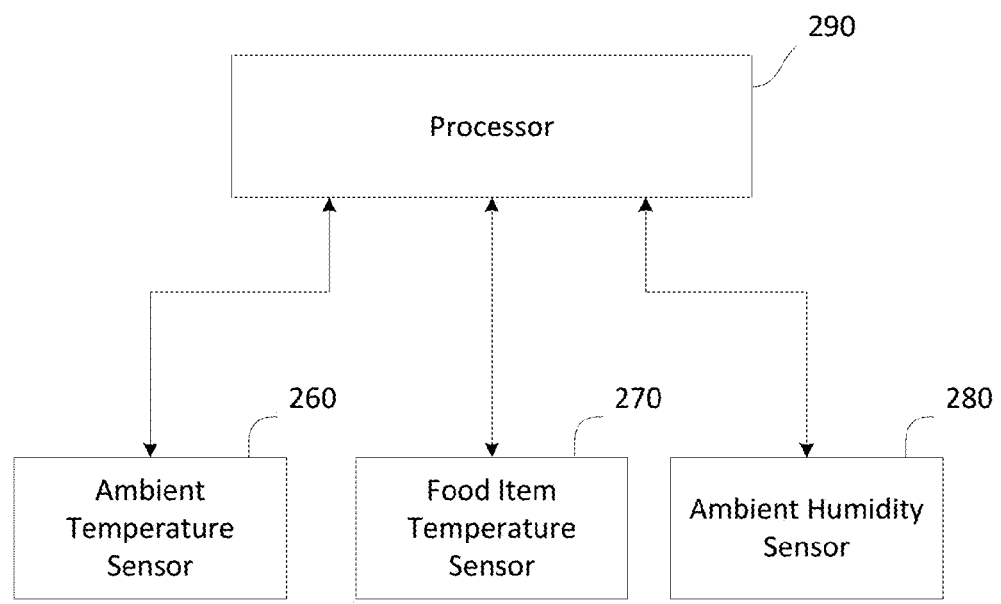
FIG. 3 is a schematic diagram illustrating exemplary environment sensors which may be used in the system of FIG. 1.

FIG. 3 is a schematic diagram of exemplary environment sensors which may be used in the system of FIG. 1. In the embodiment shown in FIG. 3, ambient thermometer 260, food thermometer 270, and ambient humidity sensor 280 are each connected to processor 290. Processor 290 may be similar or identical to processor 130 discussed above with reference to FIG. 1. In some embodiments, ambient thermometer 260, food thermometer 270, and ambient humidity sensor 280 collectively constitute the environment sensors 160 of FIG. 1.

Each of ambient thermometer 260, food thermometer 270, and ambient humidity sensor 280 is configured to sense a characteristic of the food or of the ambient environment, and to generate a signal representing a value of the sensed characteristic.

Figure 4:
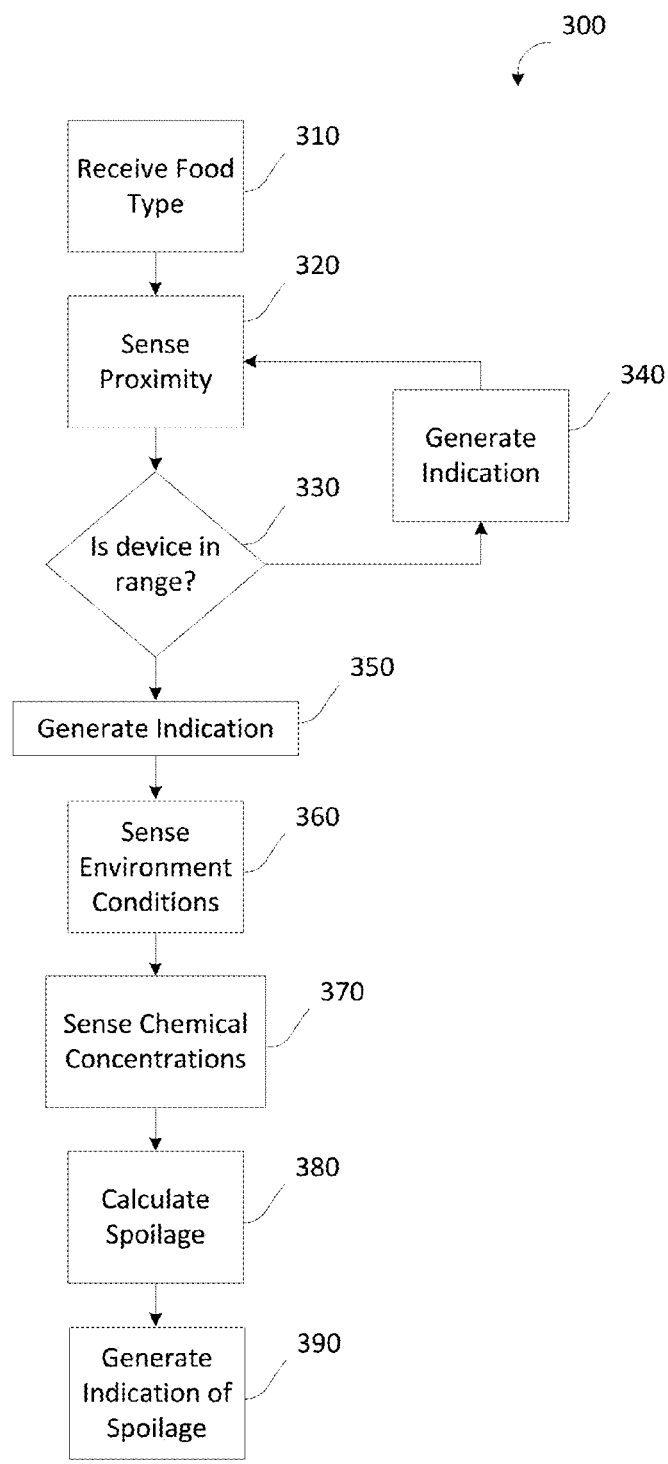
FIG. 4 is a flowchart diagram of a method of determining food spoilage using, for example, the system of FIG. 1.

FIG. 4 is a flowchart diagram of a method 300 of determining spoilage of a food item using, for example the system 100 of FIG. 1.

At 310, the system receives one or more inputs from a user at an input device. The received inputs may, for example, indicate that the system is to perform a spoilage determination. The received inputs may additionally indicate the type of food for which the spoilers determination is to be performed.

At 320, a proximity sensor of the system determines a distance between the system and the food for which spoilage determination is to be made.

At 330, a processor of the system determines whether the distance determined by the proximity sensor is within an acceptable range for performing the spoilage determination.

If the distance is determined at 330 to be too great or too small, at 340, the system generates an output with an output device indicating that the distance is not within the acceptable range. For example, the system may cause an LED to emit light. The emitted light may indicate to the user whether the distance is too great or too small.

If the distance is determined at 330 to be within the acceptable range, at 350, the system generates an output with an output device indicating that the distance is within the acceptable range. For example, the system may cause an LED to emit light, where the emitted light indicates to the user that the distance is acceptable.

At 360, the system senses environmental conditions using one or more environment sensors such as those discussed elsewhere herein. For example, the environment sensors may each generate one or more signals each indicating a value of an environment condition. The processor of the system may receive the signals from the environment sensors, generate environment data representing each of the environment conditions based on the received signals, and store the environment data in a memory of the system. In some embodiments, the system is configured to use an output device to generate an indication to the user that the environmental conditions have been sensed in response to receiving the signals from the environment sensors.

At 370, the system senses chemicals using one or more chemical sensors such as those discussed elsewhere herein. For example, the chemical sensors may each generate one or more signals each indicating a value of a concentration of the sensed chemical. The processor of the system may receive the signals from the chemical sensors, generate chemical data representing each of the chemical concentrations based on the received signals, and store the chemical data in a memory of the system. In some embodiments, the system is configured to use an output device to generate an indication to the user that the chemical concentrations have been sensed in response to receiving the signals from the chemical sensors.

At 380, the processor calculates spoilage of the food based on the environment data in the system memory, the chemical data in the system memory, and based on one or more equations or lookup tables in the memory. Spoilage calculation, according to some embodiments, is discussed in further detail below.

At 390, the system generates an indication of the spoilage calculation using the output device. For example, the system may cause an LED to emit light. The emitted light may indicate to the user whether the spoilage calculation indicates that the food is spoiled or not. In some embodiments, the indication communicates a degree of spoilage on a spoilage spectrum. In some embodiments, the indication may additionally or alternatively provide a predicted date or time of spoilage, where the prediction is calculated based on the environment data in the system memory, the chemical data in the system memory, and based on one or more equations or lookup tables in the memory.

Figure 5:
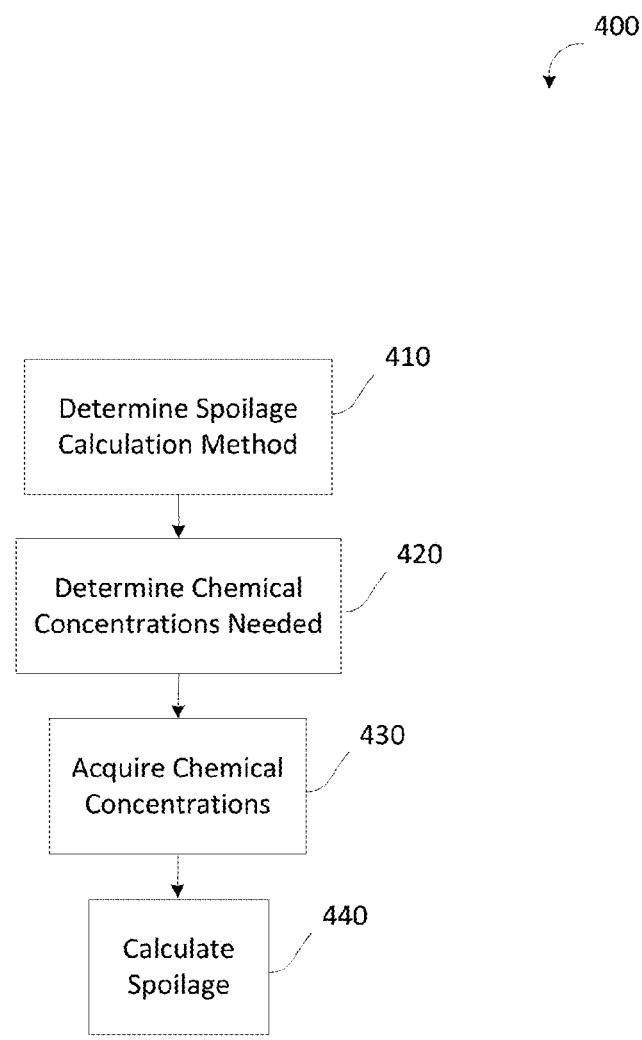
FIG. 5 is a flowchart diagram of a method of calculating food spoilage for example, as performed in the method of FIG. 4.

FIG. 5 is a flowchart diagram of a method 400 of calculating food spoilage for example, as performed in the method of FIG. 4.

At 410, based on received data indicating food type for which spoilage is to be calculated, the system accesses a variable array database in a memory storing variable arrays corresponding with multiple food types to determine a variable array corresponding with the indicated food type. For example, based on the food type, the processor may access the memory to determine a variable array corresponding with the type of food for which spoilage is to be calculated. For example, if the indicated food type is milk, the processor may access the variable array database to determine a variable array corresponding with milk. The variable array corresponding with milk indicates which variables are to be used in the calculation of spoilage for milk. For example, the variable array corresponding with milk may indicate that the calculation for spoilage of milk uses the following sensor outputs as variables: reduction sensor, oxidation sensor, alcohol sensor, milk temperature sensor, ambient temperature sensor, ambient humidity sensor, and proximity sensor.

At 420, based on the determined variable array, the system determines the variables corresponding with the indicated food. For example, if the indicated food type is milk, based on the determined variable array, the system determines that data from the following sensors is to be taken: reduction sensor, oxidation sensor, alcohol sensor, milk temperature sensor, ambient temperature sensor, ambient humidity sensor, and proximity sensor.

At 430, the system acquires data from the sensors determined at 420. For example, in response to the indicated food type being milk, the system acquires sensor data from the sensors indicated in the variable array corresponding with milk: reduction sensor, oxidation sensor, alcohol sensor, milk temperature sensor, ambient temperature sensor, ambient humidity sensor, and proximity.

In some embodiments, the sensor data acquired at 430 is the result of a statistical analysis of a set of multiple sensor readings. For example, multiple samples of reduction sensor output may be acquired, and a statistical analysis of the acquired samples may be performed to acquire sensor data for the reduction sensor. This statistical analysis may include, for example, a calculation of minimum, maximum, first sample, last sample, mean, median, standard deviation, and any other statistic. The statistical analysis may additionally or alternatively include mathematical characteristics of a linear regression of the multiple samples, such as a slope, a minimum, a maximum, and a correlation. The statistical analysis may additionally or alternatively include a mathematical function of one or more other statistical analysis results. For example, the statistical analysis may include one or more of a difference between the first and last samples, a difference between minimum and maximum, a sum of multiple statistical analysis results, a product of multiple statistical analysis results, and a ratio of multiple statistical analysis results.

At 440, the system calculates spoilage using data acquired at 430 as input variables to an equation corresponding with the indicated food type. For example, in response to the indicated food type being milk, the system accesses an equation database in a memory storing equations corresponding with multiple food types to determine an equation corresponding with milk, and using the accessed equation and the sensor data as input variables to the equation, calculates food spoilage.

In some embodiments, the system additionally or alternatively calculates an expected or predicted time or date of spoilage using data acquired at 430 as input variables to an equation corresponding with the indicated food type. For example, in response to the indicated food type being milk, the system accesses the equation database storing equations corresponding with multiple food types to determine an equation corresponding with milk, and using the accessed equation and the sensor data as input variables to the equation, calculates an expected food spoilage date or time. In some embodiments, the equation for calculating expected food spoilage date or time is the same as the equation for calculating spoilage of the food item. In embodiments where expected or predicted time of spoilage is calculated, the results of the time of spoilage calculation may be output using an output device.

In some embodiments, the equation database includes multiple linear equations corresponding with multiple food types. For example, each of the linear equations in the equation database may be represented as a number of input variables and a number of coefficients, each corresponding with one of the input variables, where the spoilage is calculated using the equation by summing the products of the variables with their corresponding coefficients. In some embodiments, each of the equations in the equation database may be represented as a number of input variables, a number of coefficients, each corresponding with one of the variables, and a number of exponents, each corresponding with one of the variables, where the spoilage is calculated using the equation by summing the products of the variables raised to their corresponding exponents with their corresponding coefficients. In some embodiments, other equations are used.

To calculate food spoilage, the system may use the sensor data as input variables and the coefficients corresponding with the input variables. For example, the sensor data acquired at 430 for each of the sensors may be multiplied by a corresponding coefficient as determined by the information in the equation database. For example, in the case of milk, the sensor data for each of the reduction, oxidation, alcohol, milk temperature, ambient temperature, and ambient humidity sensors is multiplied by a corresponding coefficient as determined by the information in the equation database corresponding with milk. The results of the products of the sensor data and their corresponding coefficients are summed, and, to determine whether or not the food is spoiled, the result of the summation is compared with a threshold, where the threshold may be accessed from a database, such as the variable array database. In some embodiments, determining whether or not the food is spoiled includes determining an age of the food item, and comparing the determined age with a spoiled age for the environment conditions, where the spoiled age may be accessed from a database, such as the variable array database. In some embodiments it an offset is also included, for example, as part of the equation.

To calculate the predicted food spoilage time, the system may use the sensor data as input variables and the coefficients corresponding with the input variables. For example, the sensor data acquired at 430 for each of the sensors may be multiplied by a corresponding coefficient as determined by the information in the equation database. For example, in the case of milk, the sensor data for each of the reduction, oxidation, alcohol, milk temperature, ambient temperature, and ambient humidity sensors is multiplied by a corresponding coefficient as determined by the information in the equation database corresponding with milk. The results of the products of the sensor data and their corresponding coefficients are summed and compared to equation data to determine, for example, an age of the food item. To calculate the predicted food spoilage time, a difference between the determined age of the food item and a spoiled age for the food item in the environment conditions is determined, where the spoiled age may be accessed from a database, such as the variable array database. In some embodiments an offset is also included, for example, as part of the equation.

The coefficients of the equations may be determined experimentally. For example, chemical and environment sensor data samples may be acquired over time as a food sample spoils under varying environmental conditions and at different distances from the food sample. The chemical, environment, and proximity sensor data samples may be arranged in a N×M sensor data matrix, where M is the number of chemical, environment, and proximity sensor data and N is the number of samples. To determine the coefficients of the equations, the pseudo-inverse of the sensor data matrix may be multiplied by a 1 by N matrix of sampling times.

In some embodiments, either or both of the variable array database and the equation database may be updated using an electronic communication network.

In some embodiments, the system may be configured to transmit via an electronic communication network data collected. For example, if the system is used to determine spoilage of a food item, the acquired sensor data along with an indication of the age of the food received via an input device of the system, may be transmitted to a database, where it may be used to modify information for either or both of the variable array database and the equation database. As a result, the information of the variable array database and the equation database of each of many systems may be updated and revised according to the sampling information received from the many systems, for example, as described above.

Figure 6:
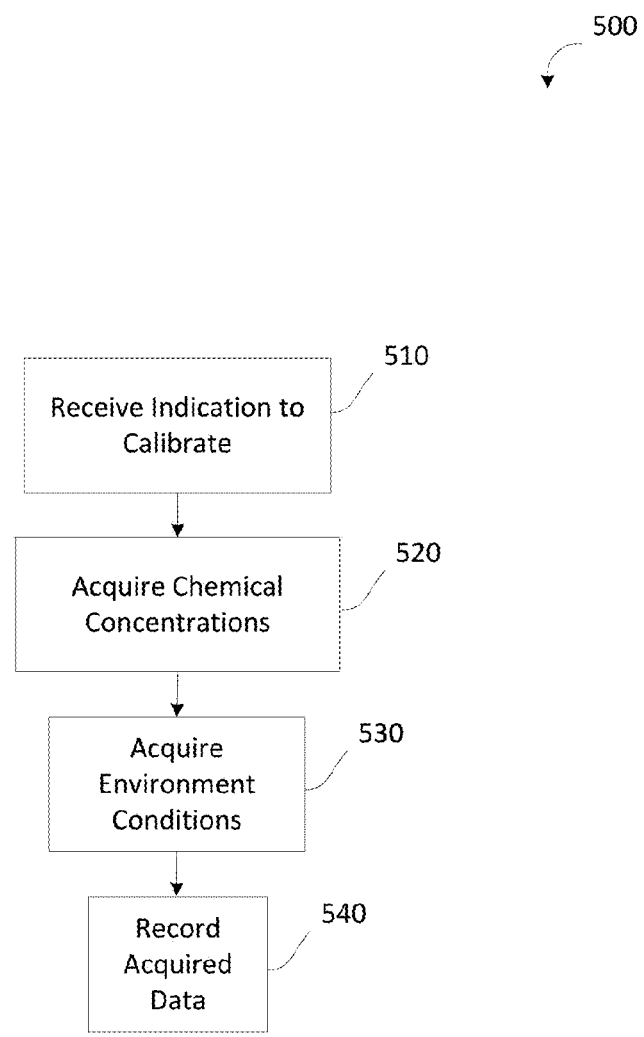
FIG. 6 is a flowchart diagram of a method of calibrating a food storage environment using a food spoilage determination device, such as the system of FIG. 1.

FIG. 6 is a flowchart diagram of a method 500 of calibrating a food storage environment using a food spoilage determination device, such as the system of FIG. 1.

At 510, the system receives one or more inputs from a user at an input device. The received inputs may, for example, indicate that the system is to perform a food storage environment calibration. The received inputs may additionally indicate one or more aspects of the food storage environment to calibrate.

At 520, in response to the inputs, using one or more chemical sensors, the system acquires one or more values of chemical concentrations. For example, the system may acquire one or more chemical values for concentrations of chemicals indicated by the inputs.

At 530, in response to the inputs, using one or more environment sensors, the system acquires one or more values of environment aspects. For example, the system may acquire one or more environment values for aspects of the environment indicated by the inputs.

At 540, the system stores the chemical values and the environment values in a memory. The chemical values and the environment values may, for example, represent ambient conditions of the food storage environment.

In some embodiments, the stored ambient conditions may be used in conjunction with environment data and chemical data in a spoilage determination process. For example, environment data and chemical data acquired as part of a spoilage determination process may be compared with the environment values and chemical values acquired as part of a calibration. In some embodiments, environment values and chemical values acquired as part of calibration are subtracted from environment data and chemical data acquired as part of a spoilage determination process.

Figure 7:
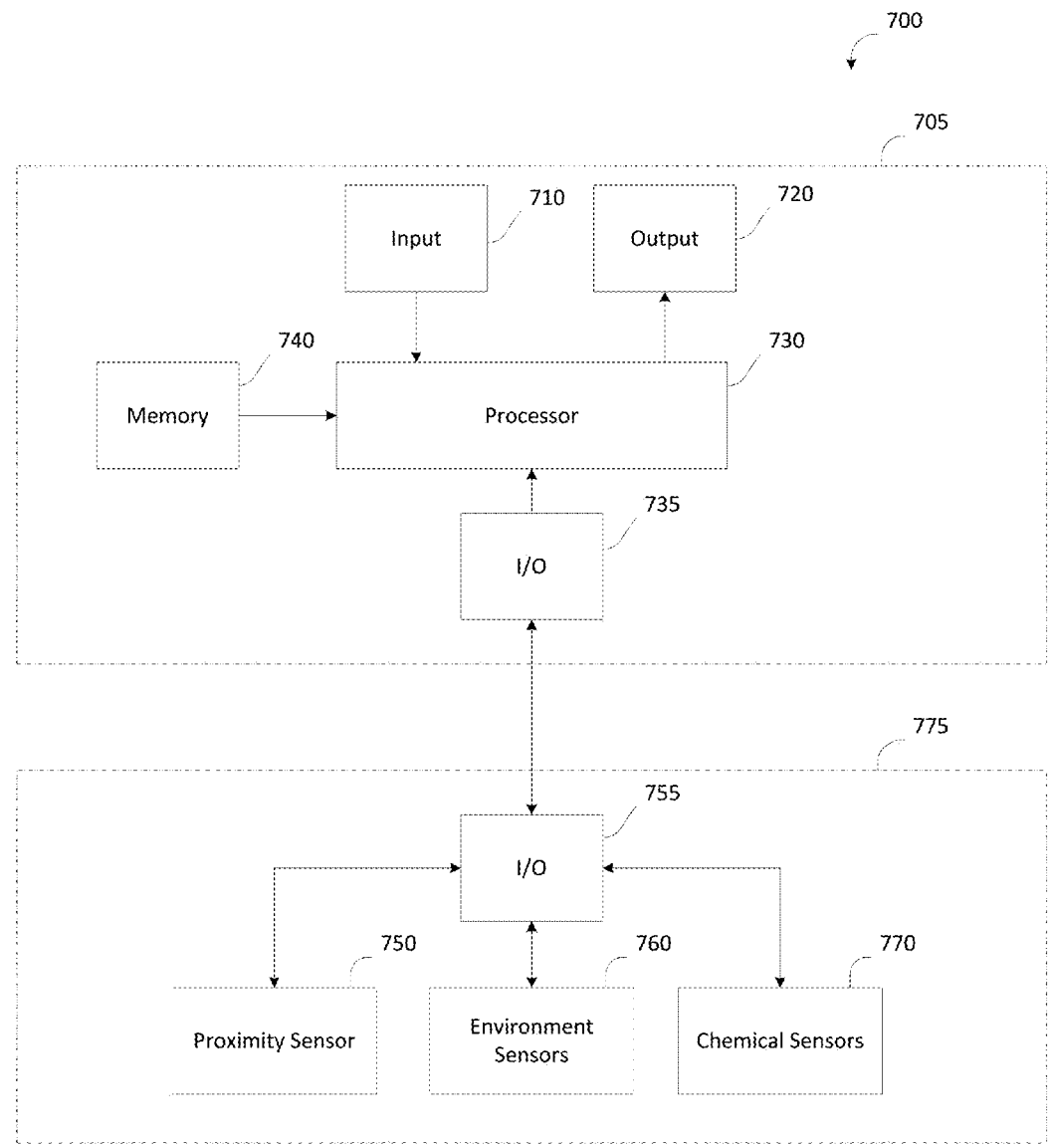
FIG. 7 is a schematic diagram of a food spoilage determination system according to another embodiment.

FIG. 7 is a schematic diagram of a food spoilage determination system 700 according to another embodiment. Food spoilage determination system 700 has characteristics similar input source 110 food spoilage determination system 100 of FIG. 1, and may be configured to perform any of the functions described herein with reference to food spoilage determination system 100.

Food spoilage determination system 700 includes input source 710 and output device 720, each connected with processor 730, which is in electrical communication with memory 740, proximity sensor 750, environment sensors 760, and chemical sensors 770. Input source 710 may have characteristics similar or identical to the input source 110 of food spoilage determination system 100. Output device 720 may have characteristics similar or identical to the output device 120 of food spoilage determination system 100. Processor 730 may have characteristics similar or identical to the processor 130 of food spoilage determination system 100. Memory 740 may have characteristics similar or identical to the memory 140 of food spoilage determination system 100. Proximity sensor 750 may have characteristics similar or identical to the proximity sensor 150 of food spoilage determination system 100. Environment sensors 760 may have characteristics similar or identical to the environment sensors 160 of food spoilage determination system 100. Chemical sensors 770 may have characteristics similar or identical to the chemical sensors 170 of food spoilage determination system 100.

In some embodiments, input source 710, output device 720, processor 730, and memory 740 are incorporated in a first device 705, and proximity sensor 750, environment sensors 760, and chemical sensors 770 are incorporated in a second device 775.

In the embodiment shown, first device 705 includes a communications module 735 configured to bidirectionally communicate with processor 730. In addition, second device 775 includes a communication module 755 configured to bidirectionally communicate with each of proximity sensor 750, environment sensors 760, and chemical sensor 770. First device 705 and second device 775 are configured to bidirectionally communicate via communication modules 735 and 755. In some embodiments, communication module 735 and 755 are configured to bidirectionally communicate wirelessly. In some embodiments, communication module 735 and 755 are configured to bidirectionally communicate with a wired connection, such as a mini USB connection. In some embodiments, first device 705 is a cell phone or comprises a cell phone.

Though the present invention is disclosed by way of specific embodiments as described above, those embodiments are not intended to limit the present invention. Based on the methods and the technical aspects disclosed above, variations and changes may be made to the presented embodiments by those skilled in the art without departing from the spirit and the scope of the present invention.

What is claimed is:

1. A food spoilage determination device, comprising:
an input device configured to receive an input from a user, the input indicating a food type,
a processor programmed to receive a representation of the input from the input device, to select one or more aspects of the environment based on the food type indicated by the input, to select one or more chemical concentrations of the environment based on the food type indicated by the input and to determine a plurality of coefficients based on the food type indicated by the input;
an output device configured to generate outputs for the user based on output signals received from the processor;
a proximity sensor configured to determine a distance to a target and to communicate a first output signal to the processor based on the distance, wherein the processor is further programmed to determine whether the distance is within an acceptable range for performing a spoilage determination, and to cause the output device to generate an output indicating whether the distance is within the acceptable range;
one or more environment sensors configured to determine one or more aspects of an environment of the target and to communicate one or more second output signals to the processor based on the one or more determined aspects, wherein the one or more determined aspects correspond with the one or more aspects of the environment selected by the processor based on the food type indicated by the input, and
one or more chemical sensors configured to determine one or more concentrations of one or more chemicals in the environment of the target and to communicate one or more third output signals to the processor based on the one or more determined concentrations, wherein the one or more determined concentrations of the one or more chemicals provide an indication of whether the target has spoiled, and wherein the one or more determined concentrations correspond with the one or more chemical concentrations of the environment selected by the processor based on the food type indicated by the input;
wherein the processor is further programmed to calculate a numeric indication of food spoilage of the target based on the first input signal, the one or more second output signals, the one or more third output signals, and the coefficients determined by the processor based on the food type indicated by the input,
wherein the processor is further programmed to compare the numeric indication of food spoilage with a threshold, and
wherein the processor is further programmed to generate a spoilage indication with the output device, wherein the spoilage indication indicates whether the target is spoiled.

2. The device of claim 1, wherein the chemical sensors comprise a reduction sensor, and oxidation sensor, and an ammonia sensor.

3. The device of claim 2, wherein the chemical sensors comprise an alcohol sensor.

4. The device of claim 1, wherein the environment sensors comprise an ambient temperature sensor, a target temperature sensor, and an ambient humidity sensor.

5. The device of claim 1, wherein the processor is further programmed to determine an equation based on the food type indicated by the input, and wherein the processor is programmed to calculate the numeric indication of the food spoilage of the target based on the first output signal, the one or more second output signals, the one or more third output signals, the coefficients determined by the processor based on the food type indicated by the input, and the equation based on the food type indicated by the input.

6. The device of claim 1, wherein the processor is further programmed to generate a distance based on the first output signal and to communicate the generated distance to a database using a communication network, wherein the processor is further programmed to generate one or more aspects of the environment based on the one or more second output signals and to communicate the generated one or more aspects to the database using the communication network, and wherein the processor is further programmed to generate one or more chemical concentrations of the environment based on the one or more third output signals and to communicate the generated one or more chemical concentrations to the database using the communication network.

7. A food spoilage determination system, comprising:
a first device, comprising:
an input device configured to receive an input from a user, the input indicating a food type;
a processor programmed to receive a representation of the input from the input device, to select one or more aspects of the environment based on the food type indicated by the input, to select one or more chemical concentrations of the environment based on the food type indicated by the input and to determine a plurality of coefficients based on the food type indicated by the input, and
an output device configured to generate outputs for the user based on output signals received from the processor; and
a second device, comprising:
a proximity sensor configured to determine a distance to a target and to communicate a first output signal to the processor of the first device based on the distance, wherein the processor of the first device is further programmed to determine whether the distance is within an acceptable range for performing a spoilage determination, and to cause the output device to generate an output indicating whether the distance is within the acceptable range, one or more environment sensors configured to determine one or more aspects of an environment of the target and to communicate one or more second output signals to the processor of the first device based on the one or more determined aspects, wherein the one or more determined aspects correspond with the one or more aspects of the environment selected by the processor of the first device based on the food type indicated by the input, and one or more chemical sensors configured to determine one or more concentrations of one or more chemicals in the environment of the target and to communicate one or more third output signals to the processor of the first device based on the one or more determined concentrations, wherein the one or more determined concentrations of the one or more chemicals provide an indication of whether the target has spoiled, and wherein the one or more determined concentrations correspond with the one or more chemical concentrations of the environment selected by the processor of the first device based on the food type indicated by the input wherein the processor of the first device is further programmed to calculate a numeric indication of food spoilage of the target based on the first input signal, the one or more second output signals, the one or more third output signals, and the coefficients determined by the processor based on the food type indicated by the input, wherein the processor of the first device is further programmed to compare the numeric indication of food spoilage with a threshold, and wherein the processor of the first device is further programmed to generate a spoilage indication with the output device of the first device, wherein the spoilage indication indicates whether the target is spoiled.

8. The system of claim 7, wherein the chemical sensors comprise a reduction sensor, and oxidation sensor, and an ammonia sensor.

9. The system of claim 8, wherein the chemical sensors comprise an alcohol sensor.

10. The system of claim 7, wherein the environment sensors comprise an ambient temperature sensor, a target temperature sensor, and an ambient humidity sensor.

11. The system of claim 7, wherein the processor of the first device is further programmed to determine an equation based on the food type indicated by the input, and wherein the processor of the first device is programmed to calculate the numeric indication of the food spoilage of the target based on the first output signal, the one or more second output signals, the one or more third output signals, the coefficients determined by the processor of the first device based on the food type indicated by the input, and the equation based on the food type indicated by the input.

12. The device of claim 7, wherein the processor of the first device is further programmed to generate a distance based on the first output signal and to communicate the generated distance to a database using a communication network, wherein the processor of the first device is further programmed to generate one or more aspects of the environment based on the one or more second output signals and to communicate the generated one or more aspects to the database using the communication network, and wherein the processor of the first device is further programmed to generate one or more chemical concentrations of the environment based on the one or more third output signals and to communicate the generated one or more chemical concentrations to the database using the communication network.

13. The system of claim 7, wherein the first device comprises a cell phone.

14. The system of claim 7, wherein the first device and the second device are configured to electronically communicate with one another.

15. The system of claim 14, wherein the first and second devices are configured to communicate over a wireless communication connection.

16. The system of claim 14, wherein the first and second devices are configured to communicate over a wired communication connection.

* * * * *